United States Patent
List

(10) Patent No.: US 8,814,809 B2
(45) Date of Patent: Aug. 26, 2014

(54) TEST UNIT FOR USE IN A TEST DEVICE AND TEST SYSTEM

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/292,815

(22) Filed: Nov. 9, 2011

(65) Prior Publication Data

US 2012/0116250 A1    May 10, 2012

Related U.S. Application Data

(63) Continuation of application No. PCT/EP2010/056306, filed on May 9, 2010.

(30) Foreign Application Priority Data

May 9, 2009   (EP) ..................................... 09159834

(51) Int. Cl.
*A61B 5/00*       (2006.01)

(52) U.S. Cl.
USPC ........................................................ 600/583

(58) Field of Classification Search
USPC ........... 600/583, 584; 606/181–183; 422/424, 422/87; 436/130, 169, 3
See application file for complete search history.

(56) References Cited

U.S. PATENT DOCUMENTS

| | | | | |
|---|---|---|---|---|
| 5,447,688 | A * | 9/1995 | Moore | .......................... 422/424 |
| 7,169,117 | B2 * | 1/2007 | Allen | ............................ 600/584 |
| 2002/0052618 | A1 | 5/2002 | Haar et al. | |
| 2008/0249435 | A1 | 10/2008 | Haar et al. | |
| 2010/0168617 | A1 | 7/2010 | Fuerst et al. | |

FOREIGN PATENT DOCUMENTS

| | | |
|---|---|---|
| EP | 1 346 686 A2 | 9/2003 |
| WO | 2008135628 A1 | 12/2008 |
| WO | 2008145625 A2 | 12/2008 |

OTHER PUBLICATIONS

GrafixPlastics Mylar Spec Sheet, 2007.*

* cited by examiner

*Primary Examiner* — Brian Szmal
(74) *Attorney, Agent, or Firm* — Harness, Dickey

(57) ABSTRACT

The invention concerns a test system comprising a test device which has a lancing drive and an optical measuring device, and at least one test unit that is inserted into the test device as a disposable article, preferably in a magazine. According to the invention it is proposed that the measuring device can be directly coupled to a detection element of the test unit by means of an optics adapter on the device side, where a free end of the spring-loaded optics adapter lies against the detection element in a force-locking manner.

17 Claims, 4 Drawing Sheets

TEST UNIT FOR USE IN A TEST DEVICE AND TEST SYSTEM

CROSS-REFERENCE TO RELATED APPLICATIONS

This application is a continuation of International Application No. PCT/EP2010/056306, filed May 9, 2010, which claims the benefit and priority of European Patent Application No. 09159834.2, filed May 9, 2009. The entire disclosures of the above applications are incorporated herein by reference.

BACKGROUND

The invention concerns a test unit for use in a test device for a single-use analysis of a body fluid consisting of a lancing element that can be inserted into the skin of a user and an analytical detection element that can be loaded with body fluid from the skin, which consists of a reagent layer which reacts with an analyte in the body fluid and a transparent carrier platelet coated with the reagent layer. The invention additionally concerns a test system for the corresponding processing of such test units.

Such a test system is described in International Application Publication No. WO 2007/045412, Haar et al., published Apr. 26, 2007 (see also, U.S. Patent Application Publication No. 2008/0249435, Haar et al., published Oct. 9, 2008) of the applicant in which the disposable test units are provided with non-displaceably integrated light guides in order to guide the measuring light from a measuring zone to a shaft end of a lancing component onto which a coupling part is additionally injection-moulded for mechanical coupling. In one embodiment it is proposed in this document that the optical coupling can take place at the rear side of the test field across a carrier foil which is permanently joined to the distal ends of the integrated light guides. Such an arrangement avoids a laborious sample transport due to the fact that the measurement is carried out directly in the collecting zone but at the same time results in an increased complexity of the test units that can only be used for a single measurement.

SUMMARY

Based on this, the object of the invention is to further improve the known units and systems in the prior art and in particular to specify a favourable design also for the mass production of miniaturized disposable parts with at the same time a reliable measurement value detection.

In various embodiments, the present technology provides a test unit for use in a test device for a single-use analysis of a body fluid consisting of a lancing element that can be inserted into the skin of a user and an analytical detection element that can be loaded with body fluid from the skin, which detection element consists of a reagent layer which reacts with an analyte in the body fluid and a transparent carrier plate coated with the reagent layer, wherein the detection element is attached rigidly to the lancing element and can be loaded with body fluid via a capillary channel of the lancing element, characterized in that the carrier plate forms an optical interface for photometric measurement value detection at a connecting face facing away from the reagent layer that can be brought into direct abutment with an optics adapter of the device.

The invention is based on the idea of keeping the test unit free of optical waveguides and instead to dock on a light guide structure provided in the device preferably in a force-fitting manner. Accordingly it is proposed according to the invention that the carrier plate that is preferably formed from a foil as a transparent piece of flat material forms an optical interface for photometric measurement value detection at a connecting face facing away from the reagent layer that can be brought into direct abutment with an optics adapter which is installed as a component of the test device by being pressed against it. Thus, an additional light guide structure in the disposable part is dispensed with as a result of which particular advantages are achieved with regard to the overall size which is also of importance for storing a large number of consumable units in a magazine, in addition to the reduced production costs. In this connection it should also be borne in mind that several parallel light guides may be necessary for a reliable measurement value detection which would considerably increase the dimensions. In addition no coupling between light guides on the device side and consumable side would be necessary which saves an additional lossy interface.

In order to obtain an optimal measurement signal, it was recognized as particularly important that the thickness of the carrier plate should be matched to the optical properties of the light guides in the optics adapter and in particular to their diameter, numerical aperture and distance from one another. The refractive index of the carrier plate also has to be taken into consideration. In addition it should be possible to use commercial foils as a starting material. Taking these boundary conditions into account, it is particularly advantageous when the carrier plate has a thickness of less than 500 micrometers, preferably about 200 to 300 micrometers.

For the targeted processing of very small amounts of samples taking into consideration that they are provided in a capillary-active manner, it is additionally advantageous when the carrier plate is formed as a blank from a foil and preferably has a broadside area of less than 5 $mm^2$, preferably less than 1 $mm^2$.

Both aspects of the opto-mechanical coupling can be taken into account in a particularly advantageous manner by means of the fact that the lancing element has a counter bearing for supporting a force-fitting connection between the optical interface and the optics adapter.

For a rapid and accurate lancing movement it is advantageous when the lancing element has a coupling structure that can be brought into engagement with a lancing drive of the device. Another improvement in this regard results from the fact that the lancing element has two elastic coupling arms which can be deflected in opposite directions at right angles to a lancing axis where the coupling arms can be brought out of a pre-tensioned release position into an untensioned coupling position during the lancing movement of the lancing element.

With regard to the manufacturing process, it is particularly advantageous when the lancing element is formed in one piece from sheet material as a flat formed part and is in particular etched so that no additional functional parts have to be shaped on it. It is also of particular advantage when the detection element is attached rigidly to the lancing element and can be loaded with body fluid via a capillary channel.

A configuration that is particularly advantageous also for the device coupling is created by means of the fact that the lancing element has a base part with a U-shaped contour and a needle-shaped lancing member preferably provided with a capillary channel that is moulded onto the base part.

Another aspect of the invention consists of a test system comprising a test device and at least one test unit used therein as a disposable article, wherein the measuring device can be directly coupled to the detection element of the test unit by means of an optics adapter on the device side and a free end of the preferably spring-loaded optics adapter lies in a force-locking manner against a carrier plate of the detection element in the form of a transparent piece of foil or flat material. The force lock allows compensation for manufacturing tolerances and at the same time measurement signals can be reliably picked up even during the lancing movement.

An advantageous embodiment provides in this connection that the optics adapter is supported by a return means preferably in the form of a spring and can be pressed against the detection element under a force exerted by the return means.

Another improvement is achieved in that the optics adapter is movably mounted in a drive rod of the lancing drive and that the drive rod can be coupled to the test unit preferably by means of grippers in a tension-resistant manner.

In order to firstly enable a defined mechanical coupling it is advantageous when a spring force acting in the advance direction can be applied to the optics adapter in the course of an advance movement generated by the lancing drive by means of a control unit switched in a travel-dependent manner, for the optical coupling to the detection element.

In order to directly pick up a signal on the analytical component, it is advantageous when the optics adapter has one or more light guides running side by side and when the end faces of the light guides can be connected in a butt joint to the connecting face of the carrier plate.

For a reliable measurement value detection it is advantageous when a connecting end of the optics adapter facing away from the test unit is connected in a non-displaceable manner to an opto-electronic component assembly of the measuring device.

The test unit is advantageously supported in a guide preferably in a magazine chamber, wherein the guide has an in particular arched guide track to make a form-fit between the test unit and the lancing drive in the course of a lancing movement so that an automatic mechanical coupling is achieved.

DRAWINGS

The invention is further elucidated in the following on the basis of the embodiment examples shown schematically in the drawing.

DETAILED DESCRIPTION

Figure 1:
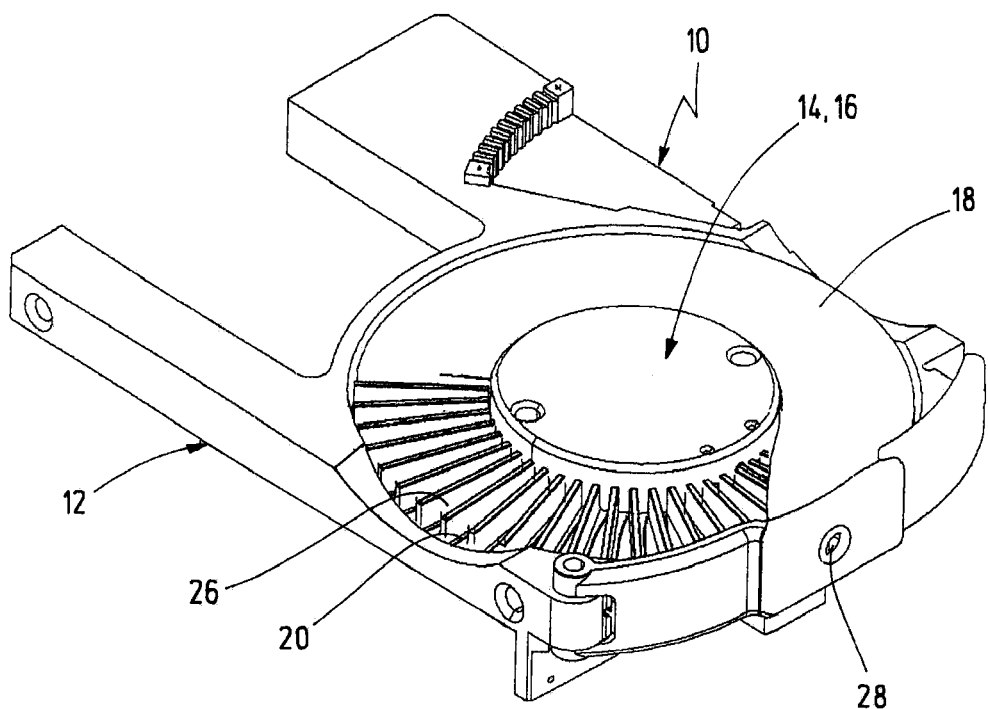
FIG. 1 shows a blood sugar test system with a magazine for test units shown partially cut open that is used therein in a perspective view.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

The test system 10 for blood sugar measurement shown in the drawing comprises a compact portable test device 12 with an incorporated lancing drive 14 and measuring device 16 as well as an exchangeable disk-shaped magazine 18 with a plurality of test units 20 located therein as consumable articles for carrying out in each case one blood sugar test, where the test units 20 in a particularly simple construction consist of a lancing element 22 with an integrated detection element 24 for sample collection and direct photometric measurement value detection. In this connection the detection element 24 is fixed in a stationary position on the lancing element 22 and thus it can be moved with the lancing element 22 during a lancing movement.

This allows even laymen to self-determine the blood sugar concentration in a fully automatic measuring process in a reliable manner with a high degree of handling convenience.

Figure 2:
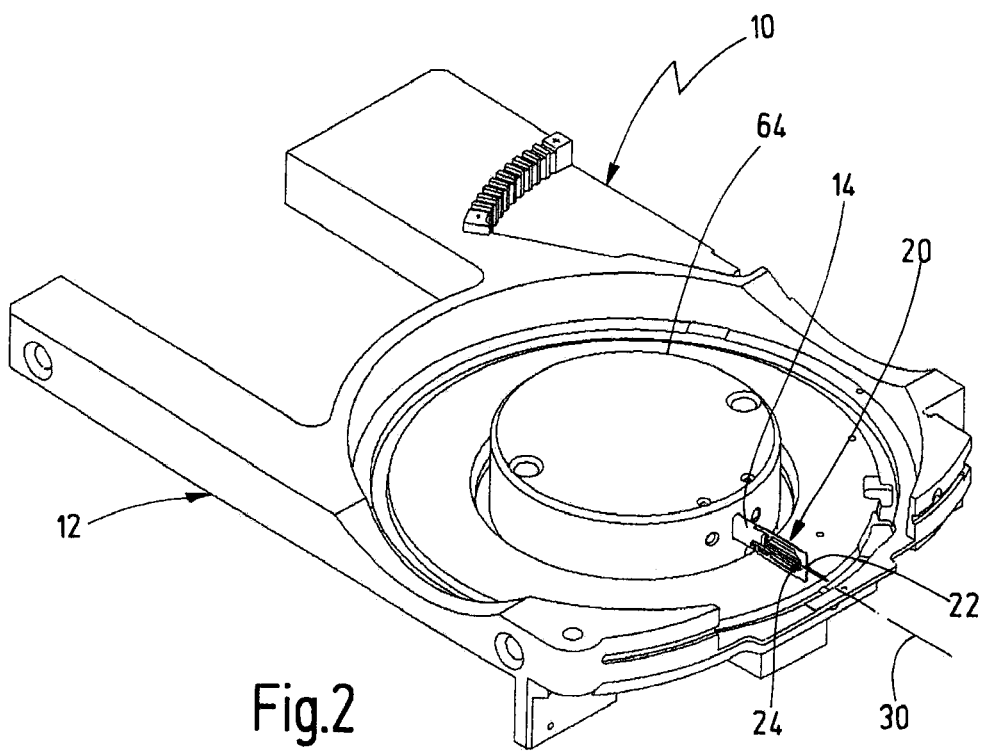
FIG. 2 shows the test system according to FIG. 1 with an activated test unit in a diagram without the magazine.

As illustrated in FIG. 1 rotating the magazine 18 allows a plurality of test units 20 in respective magazine chambers 26 to be brought successively into an active usage position with respect to a support 28 provided with a puncturing opening for positioning the finger of a user. The lancing drive 14 engaging into the actively positioned magazine chamber 26 then enables the test unit 20 to be moved back and forth along a lancing axis 30 as shown in FIG. 2. After blood collection and measurement value detection are completed, the used test unit 20 can be retracted again into the magazine chamber 26 and thus disposed of.

In general such measurements can, apart from on the finger pad, also be carried out on other parts of the body for example in the less pain-sensitive arm or stomach region where in addition to capillary blood, tissue fluid or mixtures thereof are also suitable for sample collection from the skin.

Figure 9:
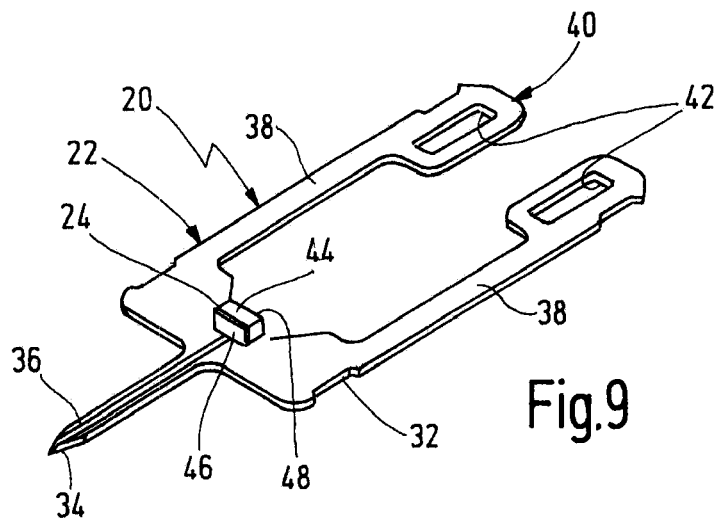
FIG. 9 shows an isolated test unit in a perspective view.

FIG. 9 shows a single test unit 20 consisting of a lancing element 22 and detection element 24. The lancing element 22 is etched in one piece from a high-grade steel sheet as a flat, shaped part and has a U-shaped base part 32 and a lancing member 34 shaped centrally and distally thereon, which is provided with a channel-shaped capillary channel 36 for blood collection during the skin puncture. The proximally projecting U-arms form coupling arms 38 which can be deflected in opposite directions at right angles to the lancing axis 30 as is elucidated in more detail in the following. A coupling structure 40 for hooking the lancing drive 14 is formed on the free ends of the coupling arms 38 where the eyes 42 form a counter bearing to support it against a spring pressure force introduced in the distal direction during the optical coupling.

As can be seen additionally in FIG. 9, the detection element 24 consists of a small flat carrier plate 44 which is firmly inserted into the lancing element 22 and is provided with a reagent layer 46 on its side facing the channel 36. This layer reacts irreversibly as a known enzymatic system to an analyte (glucose) in the blood fluid that flows against it by a change in colour that can be reflectometrically detected on the rear side through the small transparent carrier plate 44. The carrier plate 44 consisting of a transparent material with its rear side connecting face facing away from the reagent layer 46 thus forms, an optical interface for direct coupling on the device side without requiring additional light guides or optical structural components in the consumable. The carrier plate advantageously consists of a foil blank for example made of PET, PC or PMMA.

Figure 10:
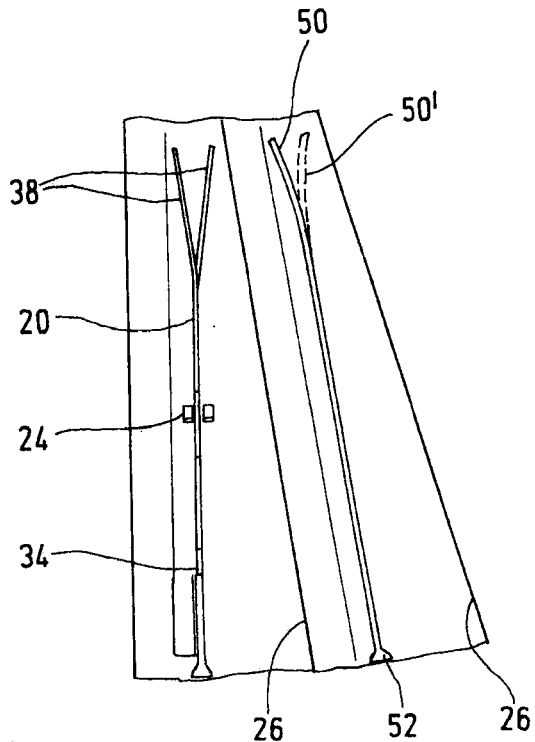
FIG. 10 shows the magazine according to FIG. 1 in a sectional top view.

FIG. 10 shows a section of two magazine chambers 26 where only the left chamber is loaded with a test unit 20. Its coupling arms 38 are held in a pretensioned starting position for mechanical coupling to the lancing drive 14. For this purpose the magazine 18 has guide tracks 50, 50' on the cover and bottom which in a proximal end section diverge in an arch shape and thus cause the coupling arms 38 to spread correspondingly. During the radial advance in the direction of the distal guide track end 52, the coupling arms 38 swing into a common guide plane in which the eyes 42 automatically hook into the lancing drive 14 while the pretensioning is released so that a substantially frictionless lancing process is possible.

Figure 3:
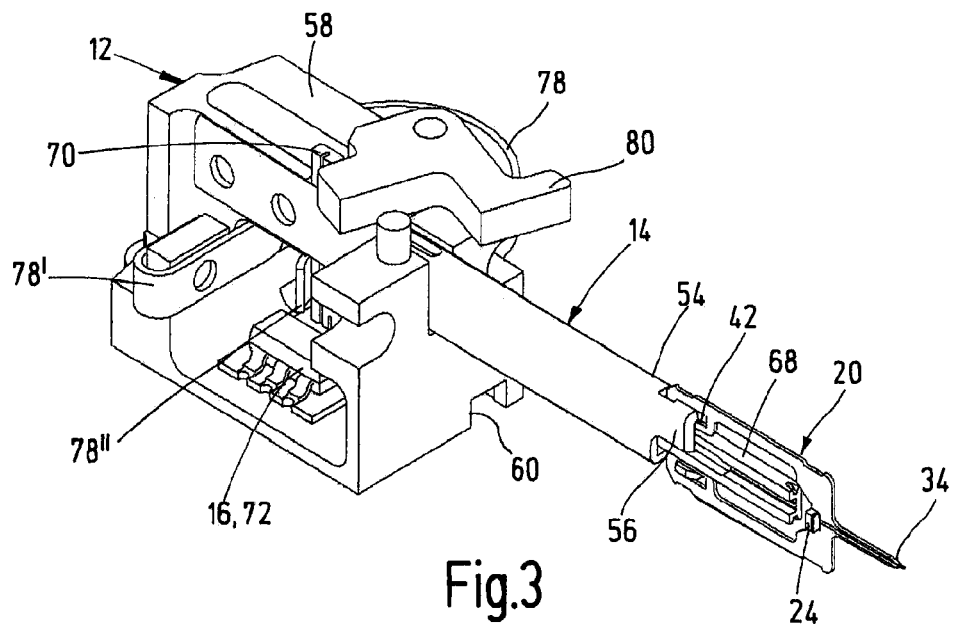
FIG. 3 shows a test unit according to FIG. 2 mechanically coupled to a lancing drive.
Figure 4:
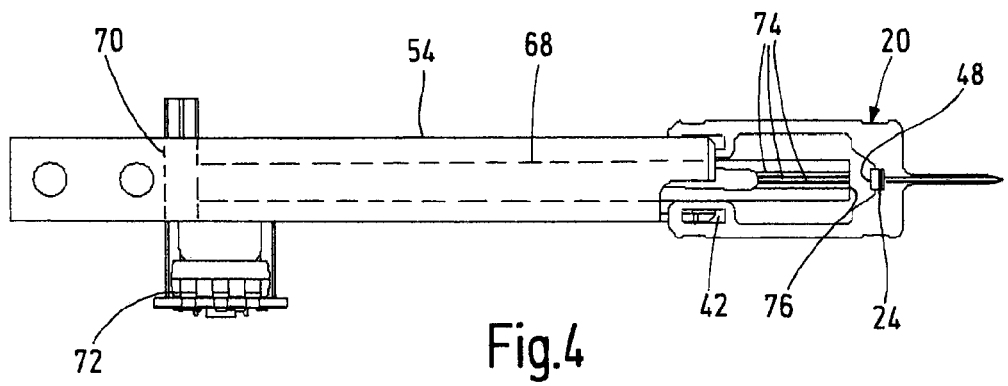
FIGS. 4 and 5 show a sectional side view and underside view of the arrangement according to FIG. 3.
Figure 5:
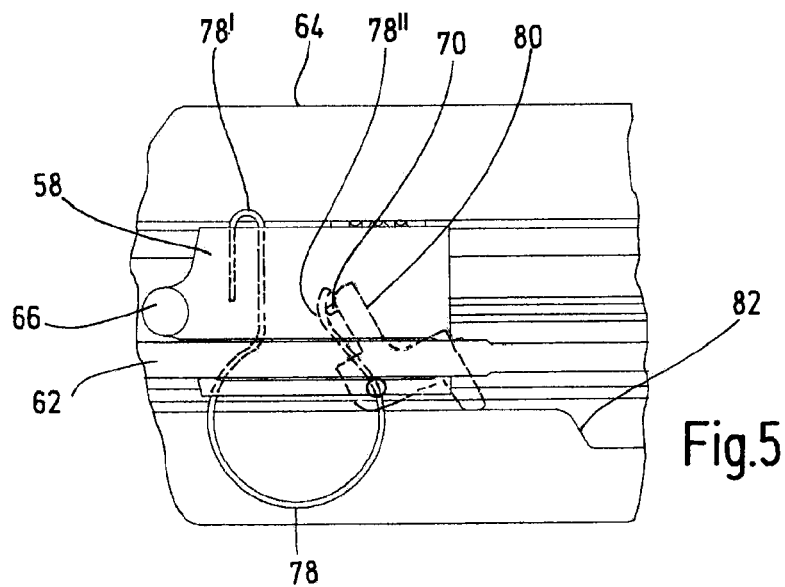

FIGS. 3 to 5 show this coupling position of the test unit 20 in a starting phase in which there is not yet any optical connection to the detection element 24. Here the gripper end 56 of a drive rod 54 of the lancing drive 14 is hooked into the eyes 42 of the test unit 20 with end play where the lancing member 34 is still located in the magazine chamber 26. The drive rod 54 is attached to a carriage 58 which can be placed onto a rail 62 in the housing dome 64 which is fixed in position in the device on a guide groove 60 that is open at the bottom and can be moved backwards and forwards thereon by means of a drive pin 66 in order to transfer the lancing movement. In this case the drive pin 66 is guided in a connecting link disk that is not shown which mediates a desired lancing profile under a motor-driven rotation.

As can be seen in particular in FIG. 2 an optics adapter 68 on the device side designed as part of the test device enables a direct optical coupling of the measuring device 16 to the detection element 24 of the test unit 20. The optics adapter 68 is mounted with limited movability in the drive rod 54 in the form of an inner rod. The optics adapter 68 is rigidly connected to an opto-electronic component assembly 72 at its T-shaped connecting end 70 that faces away from the test unit 20. This component assembly 72 contains a light emitter and light detector as part of the measuring device 16 so that a robust electrical output signal can be provided for further processing. Several light guides 74 run side by side in the optics adapter 68 for direct optical coupling to the detection element 24. These light guides end at a free distal end face 76 which can be connected in a butt joint to the connecting face 48 of the detection element 24 which is initially at a distance therefrom.

In order to be able to reliably make an optical connection by means of a force lock, a swan-neck-shaped leaf spring 78 is provided as a return means, the one spring end 78' of which is attached to the carriage 58 and the other spring end 78" of which presses against the lower arm of the T-shaped connecting end 70 of the optics adapter 68 (FIG. 3).

The pretensioning of the spring 78 is only applied during the advance movement after the gripper end 56 has hooked onto the optics adapter 68. For this purpose a control lever 80 is mounted pivotably as a control means on the carriage 58. As can be seen in FIG. 5 the control lever 80 sweeps a stepped control track 82 which runs next to the rail 62 during the lancing advance. In the starting area of control track 82 the connecting end 70 is supported by the control lever 80 so that the spring 78 does not advance the optics adapter 68.

Figure 6:
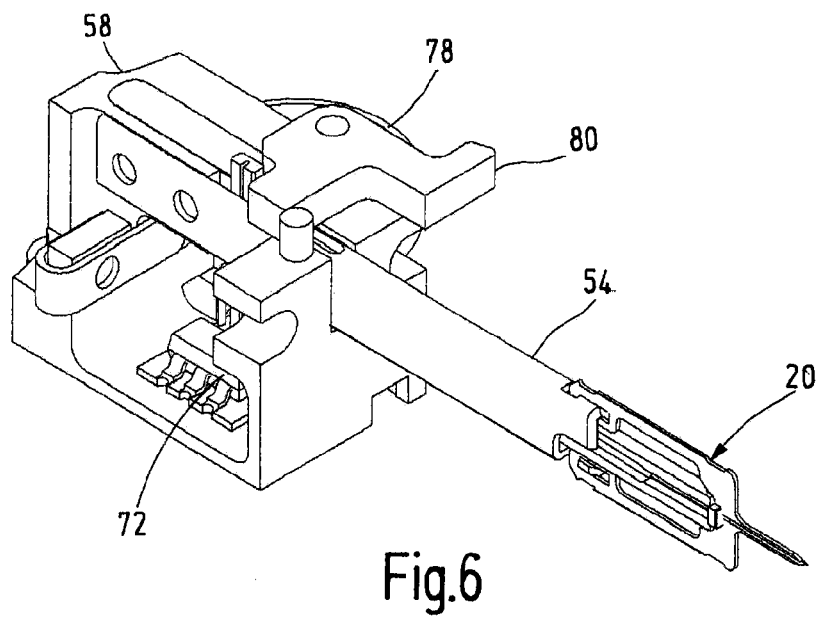
FIGS. 6 to 8 show the additionally optically coupled test unit in the advanced lancing position according to the diagrams according to FIGS. 3 to 5.
Figure 7:
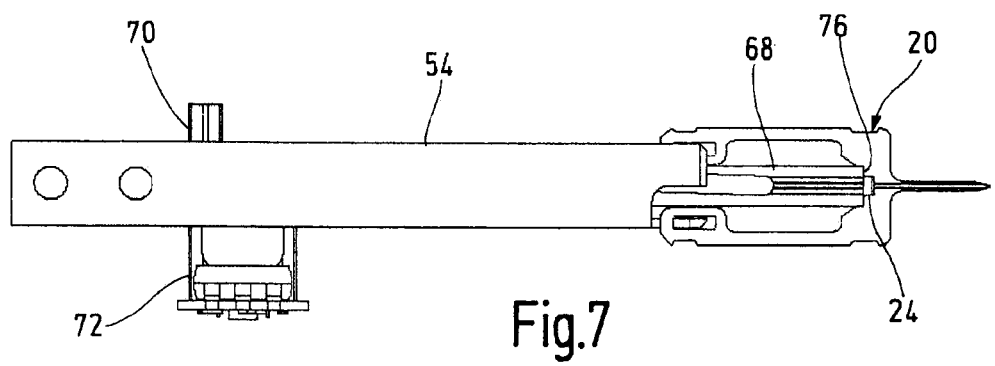
Figure 8:
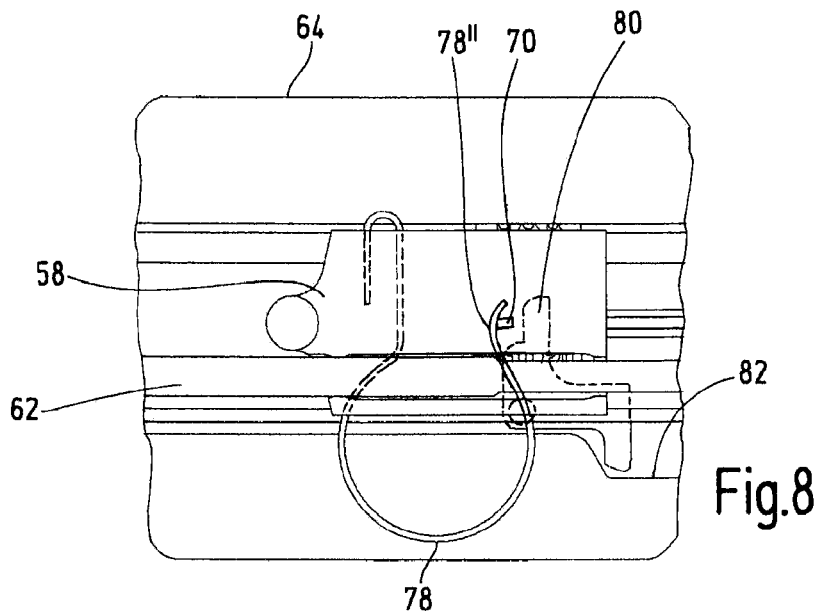

As shown in FIGS. 6 to 8 the optics adapter 68 makes a form-locking connection with the detection element 24 as soon as the control lever 80 has swept across the step of the control track 80 during the advance. The end face 76 is then pressed from the rear side against the detection element under the pretensioning force of the spring 78 in order to enable a direct coupling-in or -out of the measurement light. The gripper end 56 is thus brought into a tension-resistant connection with the elongated holes or eyes 42 which absorb the reaction force of the spring advance and thus act as counter bearings. In this manner the lancing movement can take place in the tensioned state during which a microscopic amount of blood is taken up in the skin puncture and is analyzed once.

Figure 11:
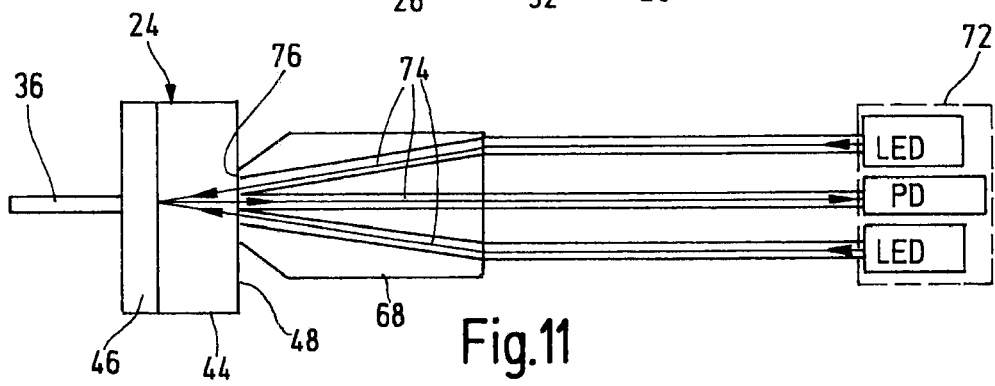
FIG. 11 shows the optical path for an optics adapter coupled to the test unit in a diagrammatic illustration.

FIG. 11 shows the optical path for the measurement in a simplified diagram. The light of two light-emitting diodes LEDs optionally having different wavelengths is beamed centrally behind the channel 36 via associated light guides 74. For a more accurate point alignment, the light guides 74 can converge towards the free end 76 in such a manner that their mutual distance from one another is less than on the radiation side. The measurement light scattered on the reagent layer 46 is also passed back onto a photodiode PD as a detector via an associated central light guide 74. In order to obtain the largest possible wanted signal and in doing so ensure a low dependency on distance tolerances, the thickness of the carrier foil 44 is limited to about 200 to 300 micrometers. At the same time the connecting face can be limited to about 0.6×0.6 mm$^2$ such that even the smallest filling amounts in the capillary channel 36 result in an adequate wetting of the reagent layer 46.

The described system 10 enables a complex measuring process to be achieved with reduced mechanical and optical components on the side of the consumable part 20 that is processed as a unit. The user only has to carry out one handling step for sample collection and measurement and does not have to be concerned about disposal of the consumable parts. The spring coupling of the optics adapter 68 in the direction of the lancing axis 30 enables tolerances to be compensated without signal losses occurring.

What is claimed is:

1. A test unit for use in a test device for a single-use analysis of a body fluid, the test unit comprising a lancing element having a coupling structure configured to be brought into engagement with a lancing drive, the lancing element is configured to be inserted into the skin of a user and an analytical detection element configured to be loaded with body fluid from the skin, the detection element comprises a reagent layer configured to react with an analyte in the body fluid and a transparent carrier plate coated with the reagent layer, wherein the detection element is attached rigidly to the lancing element and is configured to be loaded with body fluid via a capillary channel of the lancing element, and the carrier plate forms an optical interface for photometric measurement value detection at a connecting face facing away from the reagent layer that is configured to be brought into direct abutment with an optics adapter of the device.

2. The test unit according to claim 1, wherein the carrier plate has a thickness of less than 500 micrometers.

3. The test unit according to claim 2, wherein the carrier plate has a thickness of 200 to 300 micrometers.

4. The test unit according to claim 1, wherein the lancing element has a counter bearing for supporting a force-fitting connection between the optical interface and the optics adapter.

5. The test unit according to claim 1, wherein the lancing element has two elastic coupling arms configured to deflect in opposite directions crosswise to a lancing axis, where the coupling arms are brought out of a pretensioned release position into an untensioned coupling position during the lancing movement of the lancing element.

6. The test unit according to claim 1, wherein the lancing element is formed in one piece from sheet material as a flat formed part.

7. The test unit according to claim 1, wherein the lancing element has a U-shaped base part and a needle-shaped lancing member provided with a capillary channel and shaped on the base part.

8. A test unit for use in a test device for a single-use analysis of a body fluid, the test unit comprising a lancing element having a coupling structure configured to be brought into engagement with a lancing drive, the lancing element is configured to be inserted into the skin of a user and an analytical detection element configured to be loaded with body fluid from the skin, the detection element comprises a reagent layer configured to react with an analyte in the body fluid and a transparent carrier plate coated with the reagent layer, wherein the detection element is attached rigidly to the lancing element and is configured to be loaded with body fluid via a capillary channel of the lancing element, and the carrier plate forms an optical interface for photometric measurement value detection at a connecting face facing away from the reagent layer that is configured to be brought into direct abutment with an optics adapter of the device, wherein the carrier plate is formed as a blank from a foil and has a connecting face of less than 5 mm$^2$.

9. The test unit according to claim 8, wherein the carrier plate is formed as a blank from a foil and has a connecting face of less than 1 mm$^2$.

10. A test system comprising a test device which has a lancing drive and an optical measuring device, and at least one test unit inserted into the test device as a disposable article, the test unit comprising a lancing element configured to be inserted into the skin of a user and an analytical detection element configured to be loaded with body fluid from the skin and that comprises a reagent layer configured to react with an analyte in the body fluid and a transparent carrier plate coated with the reagent layer, wherein the carrier plate is formed as a blank from a foil and the measuring device is directly coupled to the carrier plate by an optics adapter of the device, wherein a free end of the optics adapter abuts against the carrier plate in a force-locking manner.

11. The test system according to claim 10, wherein the disposable article is in a magazine.

12. The test system according to claim 10, wherein the optics adapter is supported by a spring pressed against the detection element under a force exerted by the spring.

13. The test system according to claim 10, wherein the optics adapter is mounted in a drive rod of the lancing drive, wherein the drive rod is coupled to the test unit by grippers in a tension-resistant manner.

14. The test system according to claim 10, wherein a spring force acting in the advance direction is applied to the optics adapter in the course of an advance movement generated by the lancing drive by way of a control means actuated in a travel-dependent manner, for the optical coupling to the detection element.

15. The test system according to claim 10, wherein the optics adapter has one or more light guides running side by side and end faces of the light guides are connected in a butt joint to the connecting face of the carrier plate.

16. The test system according to claim 10, wherein a connecting end of the optics adapter facing away from the test unit is connected in a non-displaceable manner to an optoelectronic component of the measuring device.

17. The test system according to claim 10, wherein the test unit is supported in a guide in a magazine chamber, wherein the guide has an arched guide track to establish a form-fit between the test unit and the lancing drive in the course of a lancing movement.

* * * * *